United States Patent [19]

Nickolaus

[11] Patent Number: 4,592,912

[45] Date of Patent: Jun. 3, 1986

[54] ACHE AND PAIN RELIEVING AND PREVENTING COMPOSITION

[75] Inventor: Harriet Nickolaus, 519 E. Putnam Ave., Greenwich, Conn. 06830

[73] Assignee: Harriet Nickolaus, Greenwich, Conn.

[21] Appl. No.: 660,225

[22] Filed: Oct. 12, 1984

Related U.S. Application Data

[63] Continuation-in-part of Ser. No. 546,875, Oct. 31, 1983, abandoned.

[51] Int. Cl.$^4$ ............................................. A61K 35/78
[52] U.S. Cl. .................................................. 424/195.1
[58] Field of Search ..................................... 424/195.1

[56] References Cited

PUBLICATIONS

Chem. Abst., 61:15268, 1964.
Handbook of Non Prescription Drugs, 6th ed., pp. 355, 359 and 2360, 1980.

*Primary Examiner*—Jerome D. Goldberg
*Assistant Examiner*—John W. Rollins, Jr.
*Attorney, Agent, or Firm*—George W. Rauchfuss, Jr.

[57] ABSTRACT

A composition for the prevention of and relief of muscular aches and pains, aches caused by tension such as headaches and backaches and aches and pain caused by inflamed muscles and inflammation surrounding muscles. The composition comprises an aqueous extract of a heated composition of water and capsicum and which can contain slippery elm and myrrh gum. The composition is a non-greasy, odorless, free of sedating drugs, topically applied extract valuable for the relief and prevention of minor aches and pains.

20 Claims, No Drawings

ACHE AND PAIN RELIEVING AND PREVENTING COMPOSITION

RELATED APPLICATION

This application is a continuation-in-part of my co-pending application Ser. No. 546,875 filed Oct. 31, 1983, now abandoned.

FIELD OF THE INVENTION

The present invention relates to an extract of naturally occurring compounds that is applied topically to an individual's body for the relief of or for the prevention of muscular aches, pains, cramps and muscular spasms such as are found, for example, in overexerted muscles, misused muscles, headaches and backaches caused by muscular tension and inflammed muscles and inflammation surrounding muscles and joints.

BACKGROUND OF THE INVENTION

We live in a rich and technologically advanced society. We drive to work, we drive the children to school, we put our dirty clothes in washing machines and clothes dryers. We do not walk to work, we do not make the children walk to school, we do not have to hunt for food and we do not even lift our arms to hang the wet wash outside to dry. Hence because of our way of life, we have become weaklings physically. People are aware of how weak they are becoming and are trying to realize their physical potential and to increase their life expectancy. Today there is a great emphasis on physical activities and in a person's quest for physical fitness, muscles that have heretofore been inactive and out of condition become overexerted. These muscles begin to ache and become painful. These muscles cramp and go into spasms. Previous injuries or weaknesses in muscles, joints and limbs may also reoccur and contribute to muscular aches and pains.

We also realize how stressful our society has become. All types of medications are available for tension-related aches and pains such as headaches and backaches and the like. In our technically advanced society there are physical risks and dangers involved to one when taking oral medications and drugs for the relief of headaches and muscular pains. These drugs are sometimes addicting, sometimes they cause drowsiness, sometimes they cause stomach, intestinal and other internal upsets or disturbances. Sometimes the oral pain relievers mask the actual symptoms of an illness. Occasionally allergic reactions occur to oral medications for pain relief.

An object of this invention is to provide a method for the prevention of and for the relief of muscular aches and pains. Another object of this invention is to provide a composition of naturally derived components that can be applied topically to relieve or prevent muscular aches and pains. A further object of the present invention is to provide a composition for the relief or prevention of muscular aches and pains that has a low oral toxicity. Another further object of the present invention is to provide a topically applied composition that is not sticky or greasy on the skin and that is not odoriferous.

SUMMARY OF THE INVENTION

In accordance with the foregoing objects, the present invention briefly comprises a composition useful for the relief of or for the prevention of muscular aches and pains comprising the aqueous extract of a heated mixture of the following components: water and capsicum. Slippery elm and myrrh gum are also preferably present in the composition. Optionally the said composition contains a preservative.

DETAILED DESCRIPTION OF THE INVENTION

The composition of the present invention comprises an extract of the heated mixture of from about 92 to about 99.75% by weight water, from about 0.25 to about 6.0% by weight capsicum, up to about 1.0% by weight slippery elm and up to about 1.0% by weight myrrh gum.

Preferably, the composition of the present invention briefly comprises an extract of the heated mixture of from about 92 to about 99.75% by weight water, from about 0.25 to about 6.0% by weight capsicum, from about 0.02-1.0% by weight slippery elm and from about 0.02-1.0% by weight myrrh gum. An even more preferred embodiment of the present invention comprises an aqueous extract of a heated mixture of about 98.2% to about 98.7% by weight water, about 1.2% by weight capsicum, about 0.04% by weight slippery elm powder and about 0.08% by weight myrrh gum granules.

Preferably the extract of the present invention hereinabove set forth has added thereto a preservative and most preferably said preservative comprises benzoic acid and tetrasodium EDTA.

Capsicum is the dried ripe fruit of *Capsicum frutescens* and is commercially available in a variety of grades known as "heating units". For example, capsicum is available in heating units of 40, 60, 90, 120 and 140. The amount of capsicum employed in the compositions of this invention will depend upon the heating unit grade employed. For example, if capsicum of 120 or 140 heating unit grade is employed, the composition generally contains from about 0.25 to about 2.0% by weight capsicum. If, however, capsicum of 40, 60 or 90 heating unit grade is employed, the composition generally contains from about 2 to about 6% by weight capsicum. Capsicum suitable for use in the compositions of this invention is described for example at page 239–241 of The Dispensatory of the United States of America 25th Edition, 1955.

Slippery elm is the dried inner bark of *Ulmus fulva* (FDA Reference Disclosure No. 977001-00-5) and is described at pages 497–498 of the Dispensatory of the United States of America, 25th Edition, 1955. Myrrh gum is the oleo-gum-resin extract of various species of Commiphora and is described at pages 875 and 876 of said Dispensatory of the United States of America, 25th Edition, 1955.

The extract of the present invention is applied to a patient's skin by painting a thin coating onto the skin in the area where there is muscular ache or pain. The thin coating is allowed to dry. This thin coating should be a muscle ache or pain relieving amount. Each application of the composition of the present invention onto the patient's skin can include up to three of the aforementioned thin coatings per application. These applications can be repeated up to three or more times per day if necessary or desired.

The sensitivity of a patient's skin to the extract of the present invention will vary. The preferred number of coatings of the present invention and the preferred number of applications of the present invention will depend on the particular area of the body where the muscular aches and pains are originating and on the patient's skin type. Skin type will vary according to the area of the body, heredity and the like.

It has been found that the extract of the present invention can also be employed as a preventative of muscular aches and pains. A patient with an old injury or history of muscular cramps and spasms can use, for example, the extract of the present invention prior to physical activity that might activate the aforesaid muscular aches, pains, cramps and spasms.

As little as one topically applied coating of the aqueous extract of the present invention has been shown to provide relief from muscular aches and pains. Exactly how relief from muscular aches and pains is experienced by the use of the present invention can only be hypothesized.

The Handbook of Nonprescription Drugs, 7th Edition, page 521 describes in table form external analgesic products that are currently available commercially. All of these products rely on aromatic odors and various alcohol soluble compositions for the relief of pain. Several of these analgesics contain oils, waxes and other chemicals that leave greasy, sticky residues on the patient's skin. Everyday use of these external analgesics is unrealistic particularly when in contact with other people. These products are odoriferous and uncomfortable feeling on the patient's skin.

The present invention provides impressive results in providing relief from muscular aches and pains. The extract of the present invention is an alcohol-free aqueous solution of naturally occurring compounds. It does not stain the patient's skin or clothing when used for daytime use. The said extract does not smell. It does not emit an offensive odor. It does not leave a greasy or sticky film on the patient's skin. It does not contain sedating drugs or chemicals. It avoids the risks and dangers involved when medication is taken internally for the relief of muscular aches and pains such as addiction, drowsiness, stomach and abdominal upsets and the like. For the aforementioned reasons, the present invention provides an exceptionally valuable method for relieving muscular aches and pains, aches and pains caused by tension such as headaches and backaches and aches and pain caused by inflammed muscles and inflammation surrounding muscles. The present invention is also useful in relieving muscular aches and pains caused by sinusitis, bursitis, menstrual cramps and the like.

The preferred composition of the present invention contemplates an aqueous extract which includes from about 92 to 99.75 parts by weight sterile water, from about 0.25 to 6.0 parts by weight cayenne (*Capsicum frutescens*), from about 0.02–1.0 parts by weight slippery elm powder, from about 0.02–1.0 parts by weight myrrh gum granules or powder and a preservative mixture that is included to insure that the extract remains stable over a prolonged period of time comprising from about 0.3–0.5 parts by weight benzoic acid and from about 0.1–0.3 parts by weight tetrasodium EDTA.

Generally, the extract of the present invention is prepared by combining sterile water, distilled water, or sterile spring water and cayenne (*Capsicum frutescens*), with or without slippery elm powder, myrrh gum granules or powder, and heating to about 180°–212° F. and simmering for from about 8–13 minutes. After heating, the solution is then filtered such as, for example, through cheesecloth, or permitted to stand in a holding container or the like to remove substantially all the particulate matter.

In order to insure that the extract remains stable for a prolonged period of time, it is preferred that a preservative be added. Generally the preservative is added to the mixture after heating the mixture and cooling said mixture to about 80°–90° F. and prior to removal of the particulate matter.

Another method of preparing the extract of the present invention is to enclose each of the compounds in filter bags thereby eliminating the filtration step to remove the particulate material.

The preparation and use of the compositions of this invention is illustrated by the following examples and are not to be construed as limiting the scope of the invention.

EXAMPLE I

About 96.59 parts by weight sterile spring water, 2.89 parts by weight cayenne (*Capsicum frutescens*) described as having 90 heating units, 0.04 parts by weight slippery elm powder, and 0.08 parts by weight myrrh gum granules are mixed together in a stainless steel pot. The mixture is covered and slowly heated with occasional stirring and simmered at a temperature of about 205° to 210° F. for a period of about ten minutes. The mixture is allowed to cool to about 80°–90° F. The preservatives are then added in the amount of 0.30 parts by weight benzoic acid and 0.10 parts by weight tetrasodium EDTA. The mixture is then filtered through cheesecloth to remove substantially all particulate matter and the aqueous extract bottled.

EXAMPLE II

The aqueous extract of Example I was used by a 35 year old woman with a medical history of chronic migrane headaches. She applied said aqueous extract to her forehead and to the back of her neck. She allowed the extract to dry on her skin and then gently massaged her forehead and neck. She then applied hot, wet towels to her neck and forehead. Ten minutes later she repeated the process of applying the extract, massage and hot wet towels and within an hour her headache was greatly relieved. Presently she uses the aqueous extract of the present invention as a preventative if she feels a headache occurring and the foregoing procedure prevents her headaches.

EXAMPLE III

A 45 year old man broke his ankle 20 years ago. This old injury continued to cause pain whenever the ankle was exercised, for example, when hiking or dancing. The aqueous extract of Example I was applied to his ankle before and after strenuous exercising and the soreness that usually accompanied the physical activities was eliminated and no pain whatsoever was experienced. This man now uses the present invention as a preventative before and after any strenuous activity.

EXAMPLE IV

A 30 year old man was experiencing extreme tension due to his business. His neck and shoulders were tight and stiff from the aforementioned tension. The aqueous extract of Example I was applied to his neck and shoulders, allowed to dry and then hot wet towels were applied. This process was repeated, his muscles were loosened and his tension relieved.

EXAMPLE V

A tailor, 55 years old, strained his lower back muscles while doing sit-ups. He used a heating pad on his lower back but this did not relieve the pain that he was experiencing. He applied the aqueous extract of Example I to his back at night for one week with the use of a heating pad. At the end of this one week period, he was able to bend and move without pain.

EXAMPLE VI

Because of her heart condition, a 33 year old woman, for therapy, rides a stationary bicycle. This therapy causes her to overuse or overexert her thigh muscles, which became sore and tired. She applied the aqueous extract of Example I to her legs and with massage and applications of hot wet towels, obtained relief the same day.

EXAMPLE VII

An older woman with arthritic pain in her knee joint applies one coating of the aqueous extract of Example I to her knee and she is provided relief from said pain.

EXAMPLE VIII

A child, 10 years old, was suffering from a headache and stiffness in the neck from tension due to her schoolwork. One coating of the aqueous extract of Example I to her forehead and to the back of her neck provided her relief from the said headache within one-half hour.

EXAMPLE IX

A 43 year old woman was in extreme pain from a broken collarbone as a result of falling off a horse. Two months after this accident she still could not lift her arm because the muscles surrounding the collarbone were still in spasm. She then applied the aqueous extract of Example I to her collarbone every day for two weeks. As a result of applying the said extract, she gained much more mobility in her arm, her pain was greatly relieved and she was much more comfortable.

This same woman had another riding accident. She fell off her horse and bruised her back. After four weeks she still could not walk or drive a car. She applied the aqueous extract of Example I and after the first day was able to walk. The said extract relieved her pain and muscular spasms. She is riding again and enjoying foxhunting.

EXAMPLE X

A woman, age 32 years, had major surgery wherein a double laminectomy was performed on her lower back. Two months after said surgery, she was still experiencing lower back and neck pain. One coating of the extract of the present invention was applied to her neck and lower back. Within one-half hour she was able to walk outside substantially pain-free. The above said coating was applied after she had been having extreme difficulty walking without pain.

She now uses the composition of the present invention daily for relief of the muscular aches and pains she experiences from the surgery.

EXAMPLE XI

About 98.4 parts by weight sterile water, 1.2 parts by weight cayenne (*Capsicum frutescens*) described as having 140 heating units are mixed together in a stainless steel pot. The mixture is covered and slowly heated with occasional stirring and simmered at a temperature of about 205° to 212° F. for a period of about 10 minutes. The mixture is allowed to cool to about 80° to 90° F. Preservatives are then added in the amount of 0.3 parts by weight benzoic acid and 0.10 parts by weight tetrasodium EDTA. The mixture is then allowed to stand and substantially all particulate matter permitted to settle to the bottom of the pot. The aqueous extract is then drawn off from the top of the pot and bottled.

EXAMPLE XII

A man, age 45 years, had pain in his left thigh for about four years. Physicians thought the cause of the pain might be rheumatism. After application of two hot towels to open the pores on the painful area, the aqueous extract of Example XI was generously applied to the thigh and was rubbed in and permitted to dry. Application of hot towels and the aqueous extract of Example XI was then again repeated and rubbed in and permitted to dry. Within a period of several hours the pain was gone and remained absent for two days. Application of the hot towels followed by application of the aqueous extract of Example XI every morning for more than one month has resulted in the pain not returning.

EXAMPLE XIII

About 98.28 parts by weight sterile water, 1.2 parts by weight cayenne (*Capsicum frutescens*) described as having 140 heating units, 0.04 parts by weight slippery elm and 0.08 parts by weight myrrh gum are mixed together in a stainless steel pot. The mixture is covered and slowly heated with occasional stirring and simmered at a temperature of about 205° to 212° F. for a period of about 10 minutes. The mixture is allowed to cool to about 80° to 90° F. Preservatives are then added in the amount of 0.3 parts by weight benzoic acid and 0.10 parts by weight tetrasodium EDTA. The mixture is then allowed to stand and substantially all particulate matter permitted to settle to the bottom of the pot. The aqueous extract is then drawn off from the top of the pot and bottled.

While various embodiments of the present invention have been illustrated by means of specific examples, it is to be understood that the present invention is in no way limited thereto.

I claim:

1. The aqueous extract of a heated composition comprising from about 92 to about 99.75 weight percent sterile water, from about 0.25 to about 6.0 weight percent capsicum from *Capsicum frutescens*, up to about 1.0 weight percent slippery elm and up to about 1.0 weight percent myrrh gum.

2. The aqueous extract of claim 1 wherein the heated composition has present from about 0.02 to about 1.0 weight percent slippery elm and from about 0.02 to about 1.0 weight percent myrrh gum.

3. The aqueous extract of claim 2 wherein an effective stabilizing amount of preservative selected from the group consisting of benzoic acid and tetrasodium EDTA is present.

4. The extract of claim 2 wherein from about 0.3-0.5% by weight benzoic acid and from about 0.1-0.3% by weight tetrasodium EDTA are present as preservatives.

5. The aqueous extract of claim 1 wherein an effective stabilizing amount of preservative selected from the group consisting of benzoic acid and tetrasodium EDTA is present.

6. The extract of claim 1 wherein from about 0.3–0.5% by weight benzoic acid and from about 0.1–0.3% by weight tetrasodium EDTA are present as preservatives.

7. A method of treatment for the relief of muscular aches and pains which comprises topically applying to a patient in need thereof a muscle ache relieving amount of the extract of claim 1.

8. A method of treatment for the relief of muscular aches and pains which comprises topically applying to a patient in need thereof a muscle ache relieving amount of the extract of claim 2.

9. A method of treatment for the relief of muscular aches and pains which comprises topically applying to a patient in need thereof a muscle ache relieving amount of the extract of claim 3.

10. A method of treatment for the relief of muscular aches and pains which comprises topically applying to a patient in need thereof a muscle ache relieving amount of the extract of claim 4.

11. A method of treatment for the relief of muscular aches and pains which comprises topically applying to a patient in need thereof a muscle ache relieving amount of the extract of claim 5.

12. A method of treatment for the relief of muscular aches and pains which comprises topically applying to a patient in need thereof a muscle ache relieving amount of the extract of claim 6.

13. A method for preventing the development of muscular aches and pains comprising topically applying to a patient a muscle ache preventing amount of the extract of claim 1.

14. A method for preventing the development of muscular aches and pains comprising topically applying to a patient a muscle ache preventing amount of the extract of claim 2.

15. A method for preventing the development of muscular aches and pains comprising topically applying to a patient a muscle ache preventing amount of the extract of claim 5.

16. A method for preventing the development of muscular aches and pains comprising topically applying to a patient a muscle ache preventing amount of the extract of claim 6.

17. A method of preparing the extract of claim 1 comprising combining and mixing about 92 to about 99.75% by weight water, about 0.25 to 6.0% by weight capsicum from *Capsicum frutescens*, up to about 1.0% by weight slippery elm and up to about 1.0% by weight myrrh gum, heating said mixture at a temperature of from about 180° to 212° F. for about 8 to 13 minutes and removing substantially all particulate material from the heated mixture.

18. A method of preparing the extract of claim 1 comprising combining and mixing about 98.28% by weight water, about 1.2% by weight capsicum from *Capsicum frutescens*, about 0.04% by weight slippery elm, and about 0.08% by weight myrrh gum, heating said mixture at a temperature of from about 180° to 212° F. for about 8 to 13 minutes and removing substantially all particulate material from the heated mixture.

19. A method of claim 17 wherein from about 0.3 to 0.5% by weight benzoic acid and from about 0.1 to 0.3% by weight tetrasodium EDTA are added to the extract as preservatives.

20. A method of claim 19 wherein 0.3% by weight benzoic acid and 0.1% by weight tetrasodium EDTA are added as preservatives.

* * * * *